(12) United States Patent
Masuda et al.

(10) Patent No.: US 9,145,401 B2
(45) Date of Patent: *Sep. 29, 2015

(54) AMIDE DERIVATIVE AND USE OF THE SAME AS STABILITY INDEX OF A LULICONAZOLE PHARMACEUTICAL FORMULATION

(71) Applicants: POLA PHARMA INC., Tokyo (JP); NIHON NOHYAKU CO., LTD., Tokyo (JP)

(72) Inventors: Takaaki Masuda, Yokohama (JP); Hiroshi Yamaguchi, Tokyo (JP)

(73) Assignees: POLA PHARMA INC., Tokyo (JP); NIHON NOHYAKU CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/347,939

(22) PCT Filed: Feb. 19, 2013

(86) PCT No.: PCT/JP2013/055025
§ 371 (c)(1),
(2) Date: Mar. 27, 2014

(87) PCT Pub. No.: WO2014/041825
PCT Pub. Date: Mar. 20, 2014

(65) Prior Publication Data
US 2015/0191456 A1    Jul. 9, 2015

(30) Foreign Application Priority Data
Sep. 14, 2012  (JP) .................................. 2012-202696

(51) Int. Cl.
C07D 409/06    (2006.01)

(52) U.S. Cl.
CPC .................................. *C07D 409/06* (2013.01)

(58) Field of Classification Search
None
See application file for complete search history.

(56) References Cited

U.S. PATENT DOCUMENTS

| | | | |
|---|---|---|---|
| 5,900,488 | A | 5/1999 | Kodama et al. |
| 8,980,931 | B1 * | 3/2015 | Masuda et al. ............. 514/397 |
| 2009/0030059 | A1 | 1/2009 | Miki et al. |
| 2009/0076109 | A1 | 3/2009 | Miki et al. |
| 2009/0137651 | A1 | 5/2009 | Kobayashi et al. |
| 2010/0168200 | A1 | 7/2010 | Masuda et al. |
| 2010/0173965 | A1 | 7/2010 | Masuda et al. |
| 2010/0204293 | A1 | 8/2010 | Masuda et al. |
| 2010/0210702 | A1 | 8/2010 | Vontz et al. |
| 2012/0015997 | A1 | 1/2012 | Miki et al. |
| 2012/0022120 | A1 | 1/2012 | Kobayashi et al. |
| 2012/0149745 | A1 | 6/2012 | Kobayashi et al. |
| 2012/0329845 | A1 | 12/2012 | Masuda et al. |
| 2013/0011351 | A2 | 1/2013 | Kobayashi et al. |
| 2013/0090365 | A1 | 4/2013 | Kubota et al. |
| 2013/0096187 | A1 | 4/2013 | Kobayashi et al. |
| 2014/0080882 | A1 | 3/2014 | Masuda et al. |

FOREIGN PATENT DOCUMENTS

| | | |
|---|---|---|
| EP | 0715856 A1 | 6/1996 |
| EP | 2 005 958 A1 | 12/2008 |
| JP | 2002/114680 | 4/2002 |
| WO | WO 2007/102241 A1 | 9/2007 |
| WO | WO 2007/102242 A1 | 9/2007 |
| WO | WO 2007/102243 A1 | 9/2007 |
| WO | WO 2009/031642 | 3/2009 |
| WO | WO 2009/031642 A1 | 3/2009 |
| WO | WO 2009/031643 | 3/2009 |
| WO | WO 2009/031643 A1 | 3/2009 |
| WO | WO 2009/031644 | 3/2009 |
| WO | WO 2009/031644 A1 | 3/2009 |
| WO | WO 2010/093992 A1 | 8/2010 |
| WO | WO 2011/155640 A1 | 12/2011 |
| WO | WO 2014/041708 A1 | 3/2014 |
| WO | WO 2014/041846 A1 | 3/2014 |
| WO | WO 2014/042043 A1 | 3/2014 |
| WO | WO 2014/136282 | 9/2014 |

OTHER PUBLICATIONS

U.S. Appl. No. 14/427,890, filed Mar. 2015, Masuda et al.*
U.S. Appl. No. 14/592,695, filed Jan. 2015, Masuda et al.*
U.S. Appl. No. 14/263,293, Masuda et al.
Fleming, et al. 2010 "Nitrile-containing pharmaceuticals: Efficacious roles of the nitrile pharmacophore" *Journal of Medicinal Chemistry* 53: 7902-7917.
Niwano et al., "Efficacy of NND-502, a novel imidazole antimycotic agent, in experimental models of *Candida albicans* and *Aspergillus fumigatus* infections," *International Journal of Antimicrobial Agents*, vol. 12, pp. 221-228 (1999).

* cited by examiner

*Primary Examiner* — Michael Barker
(74) *Attorney, Agent, or Firm* — Knobbe, Martens, Olson & Bear, LLP

(57) ABSTRACT

An object is to establish an index to prepare a stable pharmaceutical formulation by specifying a related substance of luliconazole which appears depending on the type of a selected solvent in the luliconazole pharmaceutical formulation and which is different from the SE form and the Z form. Disclosed is an amide derivative of luliconazole.

1 Claim, No Drawings

AMIDE DERIVATIVE AND USE OF THE SAME AS STABILITY INDEX OF A LULICONAZOLE PHARMACEUTICAL FORMULATION

TECHNICAL FIELD

The present invention relates to an amide derivative which is useful to measure stability of luliconazole.

BACKGROUND ART

Luliconazole is an antifungal agent which is excellent in the action on fungi. At present, luliconazole is widely used as a pharmaceutical or medicine for tinea pedis and tinea corporis, and it is going to be applied also for the action on tinea unguium as well. In relation to the pharmaceutical formulation (medicament formulation) of luliconazole, it is known as problems which should be solved such that the luliconazole is converted to the stereoisomers such as the SE form or the Z form, and that the crystallization of luliconazole is caused immediately after the application (see, for example, Patent Documents 1 to 6).

PRECEDING TECHNICAL DOCUMENTS

Patent Documents

Patent Document 1: WO2007/102241;
Patent Document 2: WO2007/102242;
Patent Document 3: WO2007/102243;
Patent Document 4: WO2009/031642;
Patent Document 5: WO2009/031643;
Patent Document 6: WO2009/031644.

SUMMARY OF THE INVENTION

Technical Problem

On the other hand, when the pharmaceutical formulation of luliconazole is manufactured, such an experience has been obtained that a related substance, which is different from the SE form and the Z form, appears depending on the type of the selected solvent. Such a recognition has been obtained that the key of the manufacturing of the pharmaceutical formulation of luliconazole is to specify the related substance and clarify the relationship with respect to the pharmaceutical formulation component.

However, nothing is known at all about an amide derivative represented by the chemical formula (1). Further, nothing is known at all as well about the fact that the presence or absence of the production of this substance is an important index to select the solvent in the pharmaceutical formulation. Further, the amide derivative represented by the chemical formula (1) is a novel substance having been not described in any literature. In general, it is known that nitrile undergoes the water addition reaction caused by acid or alkali and nitrile is converted into amide. Therefore, it is considered that the substance as described above is produced by the addition of water with respect to the nitrile group of luliconazole. However, it is usually difficult to speculate that such a compound may be produced under a storage condition depending on the type of the solvent.

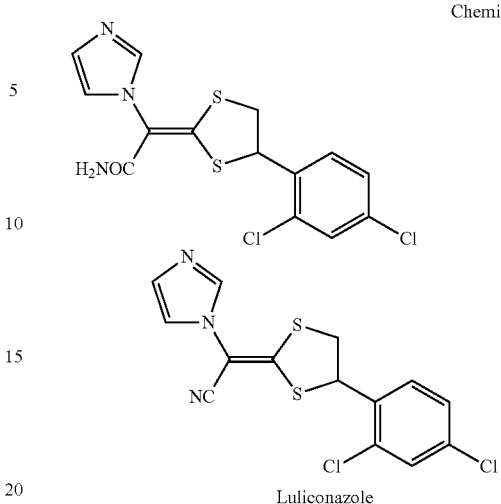

Chemical formula (1)

Luliconazole

The present invention has been made in the circumstances as described above, an object of which is to establish an index to prepare a stable pharmaceutical formulation by specifying a related substance which appears depending on the type of a selected solvent in the luliconazole pharmaceutical formulation and which is different from the SE form and the Z form.

Solution to Problem

Taking the foregoing circumstances into consideration, the present inventors have repeatedly performed diligent researches and efforts in order to seek for the structure of a related substance which appears depending on the type of a selected solvent in a luliconazole pharmaceutical formulation and which is different from the SE form and the Z form so that an index to prepare a stable pharmaceutical formulation is established. As a result, it has been found out that such a compound is the amide derivative represented by the chemical formula (1) described above, and thus the present invention has been completed. That is, the present invention is as follows.

<1> An amide derivative of luliconazole represented by the following chemical formula (1):

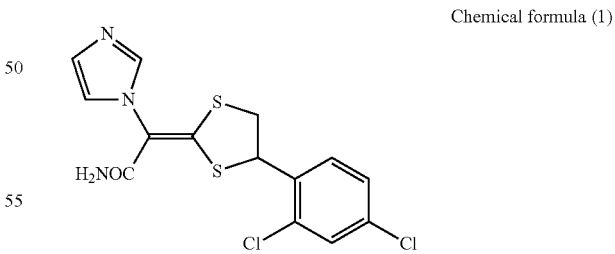

Chemical formula (1)

<2> A method for evaluating stability of a luliconazole pharmaceutical formulation, comprising:
a step of dissolving components of the luliconazole pharmaceutical formulation in a solvent; and
a step of measuring a production amount of the amide derivative as defined in <1>.

<3> The method for evaluating the stability of the luliconazole pharmaceutical formulation according to <2>, wherein it is judged that the stability of the pharmaceutical formulation is lower if the amount of production of the amide derivative under a storage condition at 40° C. or 60° C. is larger.

<4> The method for evaluating the stability of the luliconazole pharmaceutical formulation according to <2> or <3>, wherein the amide derivative is measured by means of HPLC under the following condition:
  column: ODS-2 4.6×150 mm;
  column temperature: 40° C.;
  mobile phase: solution of 0.15% sodium undecan-1-sulfonate in a mixture (water/acetonitrile/acetic acid (100) (50:49:1, v/v/v)), flow rate: 1.0 mL/min.;
  detection: 295 nm.

<5> A luliconazole pharmaceutical formulation containing a solvent, wherein a production amount of the amide derivative as defined in <1> is not more than 10% by mass with respect to a total amount of luliconazole under a storage condition at 40° C. for 6 months or at 60° C. for 3 weeks.

<6> The luliconazole pharmaceutical formulation according to <5>, wherein a polyhydric alcohol is contained as the solvent.

<7> A pharmaceutical composition containing luliconazole, wherein the pharmaceutical composition is appended with a statement of stability based on any change of a content of the amide derivative as defined in <1>.

<8> A pharmaceutical composition containing luliconazole, wherein a content of the amide derivative as defined in <1> is used as an index to evaluate a quality of the produced pharmaceutical composition.

<9> A method for selecting a pharmaceutical formulation component for a luliconazole pharmaceutical formulation, the method comprising:
  a step of selecting a component as the pharmaceutical formulation component if the amount of production of the amide derivative is small, and not selecting a component as the pharmaceutical formulation component if the amount of production is large, by using, as an index, whether a production amount of the amide derivative as defined in <1> is large or small when a component is stored at a high temperature storage condition in a state in which the component coexists together with luliconazole.

<10> The method for selecting the pharmaceutical formulation component according to <9>, wherein a high temperature storage condition is a condition at 40° C. for 6 months or at 60° C. for 3 weeks.

<11> A method for producing a pharmaceutical composition containing luliconazole, comprising a step of dissolving luliconazole in the pharmaceutical formulation components, at least one of which is selected by the method for selecting the pharmaceutical formulation component as defined in <9> or <10>.

<12> A pharmaceutical composition containing the pharmaceutical formulation component selected by the method for selecting the pharmaceutical formulation component as defined in claim <9> or <10>, and luliconazole.

<13> A method for preparing a luliconazole pharmaceutical formulation, comprising a step of substituting a solvent of the pharmaceutical formulation with another solvent if a production amount of the amide derivative as defined in <1> is large under a storage condition at 40° C. or 60° C., and adopting the solvent used for the substitution if the amount of production is low when the amount of production of the amide derivative is measured under the same storage condition in an investigating execution for preparing the luliconazole pharmaceutical formulation.

Advantageous Effects of Invention

According to the present invention, the structure of the new related substance is clarified and the index to prepare the stable pharmaceutical formulation of luliconazole is established.

DESCRIPTION OF EMBODIMENTS

<1> Indicator (Index Substance) of the Present Invention

The amide derivative of luliconazole, which is the indicator (index substance) of the present invention, is a related substance of luliconazole which appears when a specified solvent(s) is selected for the luliconazole pharmaceutical formulation. The amide derivative of luliconazole appears especially when the luliconazole pharmaceutical formulation is stored under a high temperature condition.

The substance of the present invention is the amide derivative (amide form) ([R-(E)]-α-[4-(2,4-dichlorophenyl)-1,3-dithiolan-2-ylidene]-1H-imidazole-1-acetamide) represented by the chemical formula (1). When such a compound is produced, luliconazole is treated together with water in the presence of a metal catalyst such as copper, iridium, alumina, hydroxyapatite or the like, and thus the compound can be produced. Alternatively, the compound is also obtained by allowing acid or alkali to act on luliconazole in water-containing ethanol. The amide derivative (amide form) thus obtained is purified by means of, for example, the chromatography such as silica gel column chromatography, octadecyl modified silica gel column chromatography or the like and/or the recrystallization from a mixture solution of ethyl acetate and normal hexane, ethanol, isopropanol or the like, and the amide derivative (amide form) is provided as the indicator or index substance (standard reference material). As for the indicator (index substance), it is preferable that the purity is not less than 90%.

Such a component can be confirmed by means of HPLC. When the related substance of luliconazole is confirmed, a chiral normal phase column is used in many cases in order to distinguish the isomer such as the SE form or the Z form. However, the compound of the chemical formula (1) is hardly detected under the elution condition for the chiral normal phase column. Therefore, it is preferable to perform the investigation under such a condition that a reverse phase column, which is based on the use of cation-capturing counterion such as alkylsulfonate or the like, is used. Such an analysis condition is preferably exemplified by the following. Under this condition, it is also possible to detect main related substances such as the SE form, the Z form and the like together with luliconazole.

Column: ODS-2 4.6×150 mm, column temperature: 40° C., mobile phase: solution of 0.15% sodium undecan-1-sulfonate in a mixture (water/acetonitrile/acetic acid (100) (50:49:1, v/v/v)), flow rate: 1.0 mL/min., detection: 295 nm.

<2> Method for Evaluating Pharmaceutical Formulation of the Present Invention

When the pharmaceutical formulation of luliconazole is prepared, the amide form (amide derivative) represented by the chemical formula (1) is produced during the storage at a high temperature of 40 to 60° C. depending on the type of the selected solvent. The antifungal activity of the amide form itself is low. Therefore, the production of the amide form results in the decrease in the activity of the pharmaceutical formulation. There is such a possibility that the amide form represented by the chemical formula (1) may be contained by about 10% by mass in the luliconazole pharmaceutical formulation, depending on, for example, the content of luliconazole, the type of the solvent, and the amount of the solvent.

The stability of the luliconazole pharmaceutical formulation can be evaluated by using, as the indicator (index substance), the amide form represented by the chemical formula (1) in accordance with the method for evaluating the pharmaceutical formulation of the present invention. It is possible to judge that the stability of the pharmaceutical formulation is more lower if the amount of production of the amide form represented by the chemical formula (1) is larger in the pharmaceutical formulation. Thus, it is possible to secure the stability of the pharmaceutical formulation. The following guideline can be exemplified. That is, the amount of production of the amide form is preferably not more than 10% by mass, more preferably not more than 5% by mass, much more preferably not more than 1% by mass, still much more preferably not more than 0.5% by mass, and most preferably not more than 0.1% by mass with respect to the total amount of luliconazole during the storage at 40° C. for 6 months (accelerated condition) or the storage at 60° C. for 3 weeks (severe condition), for the following reason. That is, within this range, substantially no influence is exerted on the activity of the pharmaceutical formulation. Any active pharmaceutical ingredient-related substance, which has a production amount of not more than 0.2% by mass, is not classified into the related substance according to the Pharmaceutical Affairs Law in Japan. Further, the content of the compound represented by the chemical formula (1) as described above is measured to evaluate the product, which can be also used to guarantee the quality of the product. In such a case, it is preferable that the operation for measuring the content of the compound represented by the chemical formula (1) is incorporated into the production step concerning the quality of the product. The production step concerning the quality of the product is preferably exemplified, for example, by the step of dissolving luliconazole in the solvent or the like. It is also preferable that the operation for measuring the content of the compound represented by the chemical formula (1) is incorporated into the storage step for the produced product.

<3> Method for Designing Pharmaceutical Formulation of the Present Invention

The luliconazole pharmaceutical formulation can be designed by using, as the index, the amide form represented by the chemical formula (1) of the present invention.

That is, the index is whether the amount of production of the amide form represented by the chemical formula (1) is large or small during the storage at a high temperature in a coexisting state together with luliconazole. If the amount of production of the amide derivative is large, the concerning component is not selected as the pharmaceutical formulation component. If the amount of production is small, the concerning component is selected as the pharmaceutical formulation component. Thus, it is possible to select the preferred pharmaceutical formulation component of the luliconazole pharmaceutical formulation. The basis or standard (reference), which is usable to judge whether the amount of production of the amide derivative is large or small, can be appropriately set depending on, for example, the objective pharmaceutical formulation and the method of use.

According to the method for selecting the pharmaceutical formulation component of the present invention, it has been grasped that the addition of polyhydric alcohol such as 1,3-butanediol or the like is the factor of the production of the amide form in the luliconazole pharmaceutical formulation. Other than polyhydric alcohol, it is possible to exemplify, for example, aromatic alcohol such as benzyl alcohol or the like and heterocyclic compound-based solvent such as N-methyl-2-pyrrolidone or the like as the solvent with which the amide form may be produced. If such an indicator (index substance) is increased in the prepared pharmaceutical formulation, the amount of production of the amide form as described above can be changed by substituting the solvent, especially polyhydric alcohol with another solvent.

As for the solvent as described above, polyhydric alcohol is exemplified as the solvent which acts to produce the amide form. In particular, 1,3-butanediol has an intense tendency thereof. Even in the case of polyhydric alcohol, for example, polyethylene glycol and polypropylene glycol have a weak tendency thereof. Therefore, when the amide form is considerably produced in a pharmaceutical formulation containing 1,3-butanediol, the production of the amide form can be suppressed by substituting 1,3-butanediol with polyethylene glycol and/or polypropylene glycol. In order to achieve the suppression as described above, in the case of polyethylene glycol, it is possible to exemplify that polyethylene glycol is contained preferably by 15 to 50% by mass, and polyethylene glycol is contained more preferably by 20 to 35% by mass with respect to the total amount of the pharmaceutical formulation. On the other hand, polypropylene glycol is contained preferably by 15 to 40% by mass, and polypropylene glycol is contained more preferably by 17 to 25% by mass, for the following reason. That is, if the content is excessively large, the compatibility with respect to luliconazole is deteriorated in some cases. If the content is excessively small, the effect to suppress the amide form is not recognized. When the construction as described above is adopted, then it is possible to suppress the production of the amide form, and the amount of production of the amide form can be suppressed to be not more than 10% by mass even under the accelerated condition at 40° C. for 6 months or under the severe condition at 60° C. for 3 weeks.

As described above, the production of the amide form is varied depending on the type and the amount of the pharmaceutical formulation component. Therefore in order to obtain the stable antifungal activity, it is necessary to precisely judge or discriminate whether or not the pharmaceutical formulation is adequate for luliconazole by using, as the index, the time-dependent amount of production of the amide form. The amount of production of the amide form can be used as the index for the judgment or discrimination. That is, it is possible to discriminate that the pharmaceutical formulation, which provides a larger amount of production of the amide form in the time-dependent change caused by the storage, is not adequate as the pharmaceutical formulation of luliconazole. Further, it is possible to discriminate that the pharmaceutical formulation, which provides a smaller amount of production of the amide form, is the pharmaceutical formulation adequate for luliconazole. It is affirmed that the use of the amide form for the discrimination as described above is the use of the amide form as the indicator (index substance) of the present invention. Such a mode of use can be preferably exemplified by the following mode of use. That is, the amide form of the present invention is described as the related substance, and the change of the content of the amide form, for example, under the accelerated condition or the severe condition is stated, for example, in an appended document of the pharmaceutical formulation product, wherein the probability of the stability is shown by the fact that the change is small. The pharmaceutical formulation of the medicine, which accompanies the appended document as described above, also belongs to the technical scope of the present invention. In this way, the behavior of production of the amide form is the index of the stability of the pharmaceutical formulation, and the evaluation, which is performed by utilizing the index as described above, falls under the use as the indicator (index substance).

<4> Pharmaceutical Composition of the Present Invention

In the pharmaceutical composition of the present invention, the content of luliconazole is preferably 0.1 to 20% by mass, more preferably 0.5 to 15% by mass, and much more preferably 1 to 10% by mass.

The formulation for external use, which includes, for example, liquid (solution), cream, gel, foam, spray, and ointment, can be preferably exemplified as the pharmaceutical composition of the present invention. In order to prepare the composition having the property as described above, it is possible to preferably exemplify the design of the pharmaceutical formulation as follows. That is, the components for preparing the pharmaceutical formulation are differentiated or distinguished to select the component which easily produces the amide form and the component which suppresses the production of amide form, followed by being classified into groups. When at least the component, which easily produces the amide form, is used as the pharmaceutical formulation component, the component, which suppresses the production of the amide form, is contained therein.

The pharmaceutical formulation of the present invention can contain any arbitrary component to be contained in an ordinary pharmaceutical composition, other than luliconazole and the pharmaceutical formulation component selected by the method for selecting the pharmaceutical formulation component of the present invention. Such an arbitrary component can be preferably exemplified, for example, by hydrocarbons including, for example, vaseline, microcrystalline wax, and liquid paraffin; silicones including, for example, dimethicone and cyclomethicone; esters including, for example, spermaceti and Japan tallow; triglycerides including, for example, olive oil, beef tallow, and coconut oil; non-ionic surfactants including, for example, polyoxyethylene alkyl ether, polyoxyethylene hydrogenated castor oil, and polyoxyethylene sorbitan fatty acid; anionic surfactants including, for example, sodium lauryl sulfonate and sodium POE lauryl sulfonate; fatty acids including, for example, stearic acid, oleic acid, lauric acid, palmitic acid, and myristic acid; antioxidants including, for example, BHT, BHA, and tocopherol; coloring agents; lubricants; and taste/odor-correcting agents. The pharmaceutical composition (pharmaceutical formulation) can be produced by treating the foregoing components in accordance with an ordinary method.

The pharmaceutical medicament formulation or the pharmaceutical composition of the present invention is preferably used to treat or cure the disease caused by any fungus or prevent the deterioration of the disease by utilizing the characteristic of luliconazole. The disease caused by any fungus can be exemplified by tinea pedis such as athlete's foot, tinea corporis such as candidiasis and tinea versicolor, and trichophytosis of hard keratin portion such as tinea unguium. It is especially preferable to use the pharmaceutical medicament formulation or the pharmaceutical composition of the present invention for treating the disease of the hard keratin portion such as tinea unguium, because the effect thereof is remarkable. The effect of the pharmaceutical composition of the present invention is expressed on the nail especially preferably. However, the effect is also exerted on any ordinary dermatomycosis. Therefore, the pharmaceutical composition, which is directed to the dermatomycosis and which fulfills the construction of the present invention, also belongs to the technical scope of the present invention. The dermatomycosis as described above can be exemplified, for example, by the tinea pedis and the trichophytosis of the propagation in horny substance type, the trichophytosis of the propagation in horny substance type appearing, for example, in the heel and being included in the tinea pedis. As for the dermatomycosis described above, it is preferable to make the application to the trichophytosis of the propagation in horny substance type on which any ordinary agent or drug hardly exerts the effect, because the effect of the present invention remarkably arises.

The mode of use can be appropriately selected while considering, for example, the body weight, the age, the sexuality, and the symptoms or condition of the patient. However, in the case of an adult, it is preferable to administer luliconazole in an amount of 0.01 to 1 g per day in ordinary cases. Reference can be made to the amount of use of luliconazole ordinarily used for the disease caused by any fungus.

For example, in the case of any formulation for external use, it is possible to exemplify the application in an appropriate amount to the disease portion once or several times a day. It is preferable that the treatment as described above is performed every day. In particular, in the case of the tinea unguium, luliconazole as the active ingredient, which is in an amount that cannot be brought about by any ordinary pharmaceutical formulation, can be transferred into the nail. Accordingly, the tinea unguium can be cured by means of only the external administration without taking any antifungal agent for a long period of time. Further, the recurrence and the reinfection cause great problems in relation to the tinea unguium. However, it is possible to avoid the recurrence and the reinfection as described above by administering the pharmaceutical composition of the present invention for 1 week to 2 weeks after the quietness of symptoms. In such a mode, the pharmaceutical composition of the present invention has the preventive effect.

EXAMPLES

The present invention will be explained in further detail below as exemplified by Examples. However, the present invention is not limited to Examples described below.

Example 1

1 kg of luliconazole was dissolved in a solution of ethanol containing 10% water, and 10 g of silica gel was added thereto, followed by being heated and refluxed for 1 hour. After cooling, silica gel was filtrated off. An obtained filtrate was concentrated, followed by being purified by means of silica gel column chromatography to obtain 46.41 g of crude amide form product. This product was recrystallized three times from ethanol, and 2.6 g of purified product was obtained. The characteristic values thereof were as follows.

$^1$H-NMR (CDCl$_3$, ppm): 3.617 (dd, 1H), 3.639 (dd, 1H), 5.554 (dd, 1H), 6.993 (s, 1H), 7.231 to 7.311 (m, 2H), 7.447 to 7.664 (m, 3H); m.p.: 238 to 244° C.

Example 2

Luliconazole pharmaceutical preparation 1 was manufactured in accordance with a formulation shown below. That is, formulation components were heated, stirred, and solubilized, followed by being stirred and cooled to room temperature to obtain the luliconazole pharmaceutical preparation. The luliconazole pharmaceutical preparation was stored under a temperature condition at 60° C. for 3 weeks, and produced related substances were confirmed by means of the HPLC method. As a result, three peaks were confirmed other than the peak of luliconazole. The compounds corresponding to the peaks were purified by means of the column chromatography, and the structures were determined by means of NMR and the mass spectrometry. The amide form was also the index to be considered to judge the stability together with the SE form and the Z form. That is, according to this fact, it is confirmed that the amide form is the important related substance depending on the system.

HPLC condition: column: Inertsil ODS-2 4.6×150 mm, column temperature: 40° C., mobile phase: solution of 0.15% sodium undecan-1-sulfonate in a mixture (water/acetonitrile/acetic acid (100) (50:49:1, v/v/v)), flow rate: 1.0 mL/min., detection: 295 nm.

TABLE 1

| Component | % by mass |
|---|---|
| Luliconazole | 1 |
| Diisopropyl adipate | 5 |
| Benzyl alcohol | 4 |
| Polyethylene glycol 400 | 30 |
| Ethanol | 60 |

<Related Substance>

| Peak | Result of identification | Peak area ratio with respect to peak of luliconazole (%) |
|---|---|---|
| Peak 1 | SE form | 0.29 |
| Peak 2 | Z form | 0.05 |
| Peak 3 | amide form | 0.15 |

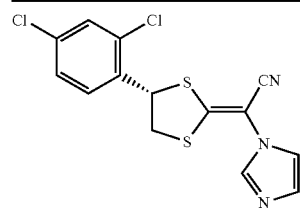

SE form

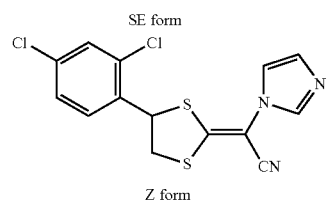

Z form

Example 3

Luliconazole pharmaceutical preparations 2 to 4 were manufactured in the same manner as in Example 2 in accordance with formulations shown below. The storage test was performed under a condition at 60° C. for 3 weeks, and the amount of the produced amide form was quantitatively measured by means of HPLC. Results are shown in Table 2. Accordingly, the following fact is confirmed. That is, the amount of production of the amide form remarkably differs depending on the type of the solvent. When the amount of production of the amide form is used as the index, it is possible to thereby estimate and discriminate the stability of the pharmaceutical formulation. That is, it is confirmed that the amide form is the important indicator (index substance) in relation to the design of the pharmaceutical formulation. It is confirmed that the condition, under which the amide form is hardly produced even under the accelerated condition and/or the severe condition, is found out by using the amide form as the index of the stability as described above, and thus it is possible to design the stable pharmaceutical formulation. It is also confirmed that the solvent component in the pharmaceutical formulation is the factor of the production of the amide form. Therefore, it is confirmed that the pharmaceutical formulation having the high stability can be manufactured by selecting the solvent which does not accelerate the production of the amide form in a time-dependent manner or which suppresses the production of the amide form. According to the results, it is also clear that such technique of the pharmaceutical formulation makes it possible to suppress the amide form to be not more than 1% by mass, more preferably not more than 0.5% by mass, and much more preferably not more than 0.1% by mass under the accelerated condition or the severe condition, for example, at 60° C. for 3 weeks. It is also confirmed that the more stable pharmaceutical formulation can be designed by fulfilling the index as described above. It is also confirmed that the solvent such as benzyl alcohol, N-methyl-2-pyrrolidone or the like is the dangerous factor in relation to the production of the amide form.

TABLE 2

| Formulation component | Pharmaceutical preparation 2 (% by mass) | Pharmaceutical preparation 3 (% by mass) | Pharmaceutical preparation 4 (% by mass) |
|---|---|---|---|
| Luliconazole | 1 | 1 | 1 |
| Crotamiton | 1 | | |
| Benzyl alcohol | | 4 | |
| N-methyl-2-pyrrolidone | | | 8 |
| Diisopropyl adipate | 5 | 5 | 5 |
| 1,3-Butanediol | 30 | 30 | 30 |
| Water | 30 | 30 | 30 |
| Ethanol | 33 | 30 | 26 |
| Amount of production of amide form (% by mass) (with respect to luliconazole) | 0.02 | 0.86 | 3.99 |

Example 4

Pharmaceutical preparations 5 and 6 were manufactured in the same manner as in Examples 2 and 3. The amide form was measured therefor in the same manner as described above after the storage at 60° C. for 3 weeks as well. Results are shown in Table 3. Accordingly, it is confirmed that 1,3-butanediol is the factor of the production of the amide form. In this way, it is confirmed that the amide form can be also used as the index to discriminate the factor to inhibit the stabilization. It is considered that the effect of polypropylene glycol to facilitate the production of the amide form is lower than that of 1,3-butanediol.

TABLE 3

| Formulation component | Pharmaceutical preparation 5 (% by mass) | Pharmaceutical preparation 6 (% by mass) |
|---|---|---|
| Luliconazole | 1 | 1 |
| Polypropylene glycol* | | 20 |
| Benzyl alcohol | 4 | 4 |
| Diisopropyl adipate | 5 | 5 |
| 1,3-Butanediol | 30 | |
| Water | 30 | 30 |
| Ethanol | 30 | 40 |
| Amount of production of amide form (with respect to luliconazole) (% by mass) | 0.86 | 0.32 |

*Average molecular weight is 2000.

Example 5

Pharmaceutical preparation 7 was manufactured in accordance with a formulation shown below. Also in this case, it is confirmed that the production of the amide form is suppressed under a storage condition at 60° C. for 3 weeks. In relation thereto, it is considered that the addition of polyethylene glycol 400 may exert any influence. Accordingly, it is considered that the effect of polyethylene glycol to facilitate the production of the amide form is lower than that of 1,3-butanediol. Thus, it has been clarified that the amide form can be used as the index for evaluating the effect of addition of the additive.

TABLE 4

| Formulation component | Pharmaceutical composition 7 (% by mass) |
|---|---|
| Luliconazole | 5 |
| Propylene carbonate | 5 |
| Benzyl alcohol | 2 |
| Lactic acid | 4 |
| Polyethylene glycol 400 | 20 |
| Diethyl sebacate | 24 |
| Polyvinylpyrrolidone | 0.25 |
| Ethanol | 39.75 |
| Amount of production of amide form (with respect to luliconazole) | 0.02 (% by mass) |

INDUSTRIAL APPLICABILITY

The present invention can be applied, for example, to the design of the pharmaceutical formulation of luliconazole and the evaluation of the pharmaceutical formulation.

The invention claimed is:

1. An amide derivative of luliconazole represented by the following chemical formula (1):

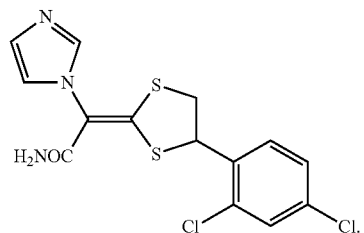

Chemical formula (1)

* * * * *